United States Patent [19]
Walker

[11] 4,076,022
[45] Feb. 28, 1978

[54] THERAPEUTIC FOOT AND LEG PROTECTOR

[76] Inventor: James Walker, 6 Pine Tree Drive, Stamford, Conn. 06906

[21] Appl. No.: 752,529

[22] Filed: Dec. 20, 1976

[51] Int. Cl.² ............................................. A61B 19/00
[52] U.S. Cl. ................................... 128/149; 128/153; 128/68.1; 128/82.1
[58] Field of Search ............... 128/149, 82.1, DIG. 15, 128/171, 80 R, 80 H, 153, 68.1

[56] References Cited

U.S. PATENT DOCUMENTS

| 2,911,657 | 11/1959 | Streeter | 128/149 UX |
| 3,011,494 | 12/1961 | McGowan | 128/153 |

FOREIGN PATENT DOCUMENTS

| 940,840 | 6/1948 | France | 128/149 |

*Primary Examiner*—Lawrence W. Trapp

[57] ABSTRACT

A therapeutic foot and leg protector comprises a rigid outer shell having a soft protective liner disposed therein. The protector is perforated in its heel portion to allow air to enter the shell and circulate about the heel of a patient. The shell is made with a built-up support section to raise the shell above the general level of the bed, so that none of the perforations in the heel become blocked. In other words, the support section will facilitate a freer circulation of air about the heel of the patient, to effect a more rapid healing of heel sores. The liner has straps that project through slots in the shell and wrap about the foot and leg of the patient. This provides for the integral securement of both the liner and shell to the leg, while allowing the liner to be a separate element. A built-up ridge section in the heel portion of the shell prevents the heel of the patient from coming into contact with the shell. This will possibly prevent injury to the heel of the patient or the blocking of the perforations in the heel portion of the shell.

10 Claims, 3 Drawing Figures

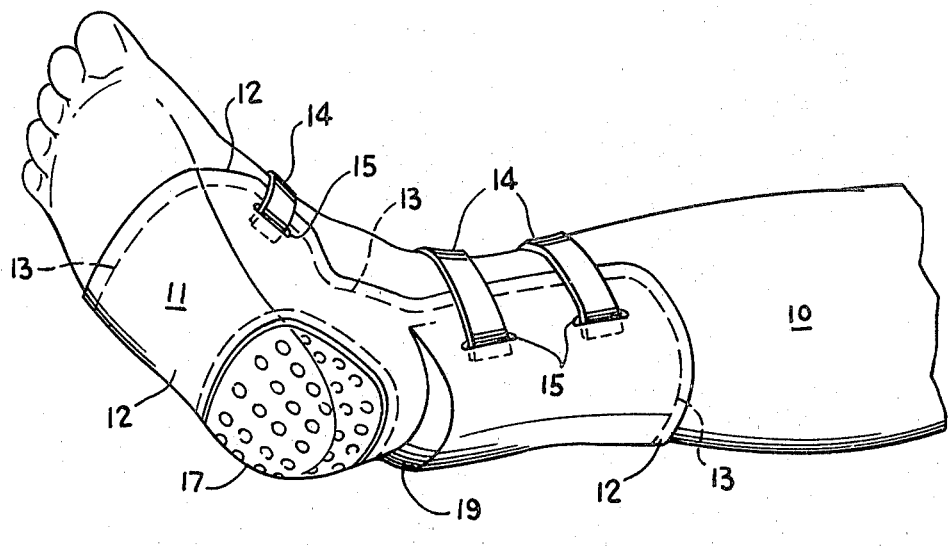
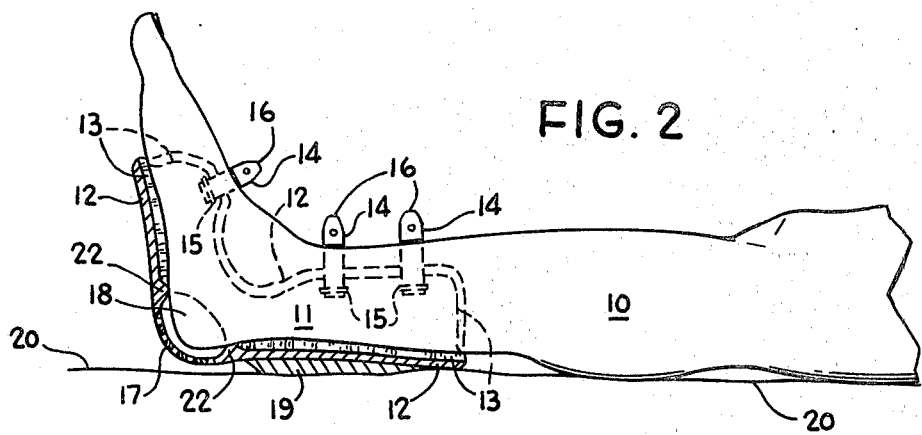
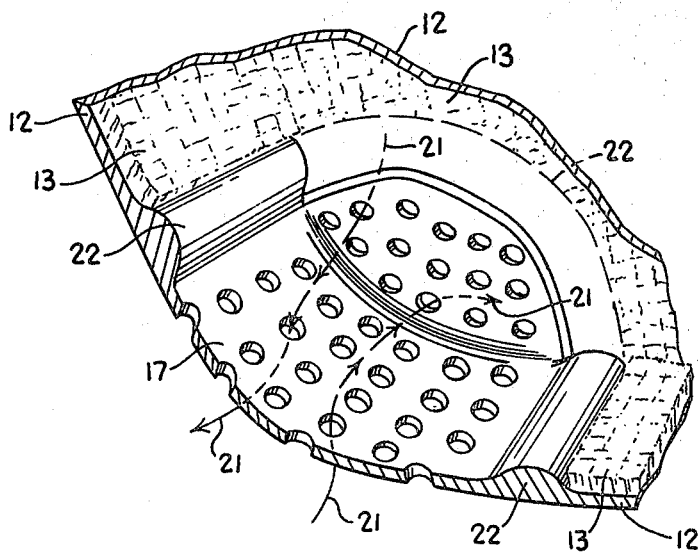

THERAPEUTIC FOOT AND LEG PROTECTOR

The invention pertains to foot and leg protective devices and more particularly to foot and leg protectors which prevent or allow for the quick healing of heel sores.

BACKGROUND OF THE INVENTION

Heretofore, many different foot and leg devices have been proposed for the cure or prevention of heel sores. These sores are known more specifically as decubitutus sores, and generally form by frictional irritation between the heel of a bed-ridden patient and the bed linens.

Some of these prior devices can be seen in the patents granted to:

A. RAGOT et al U.S. Pat. No. 940,840; France Issued: June 7, 1948;

G. W. STREETER III U.S. Pat. No. 2,911,657 Issued: Nov. 10, 1959; and

E. HOLY, Jr. U.S. Pat. No. 3,511,233 Issued: May 12, 1970.

These prior devices all suggest isolating the heel of the patient from the bed surroundings by a protective shielding or foot-like structure. Also, these devices suggested that aeration should be provided to the heel to aid the recuperative process.

All the aforementioned devices have recesses or perforations to provide aeration. However, because they rest upon the bed, or are used for walking, the perforations are very often blocked. This blockage seriously impairs the proper circulation of air about the heel.

The present invention was conceived as a protector which would overcome this drawback, while adding additional improvements for supporting the heel and leg in a better manner.

SUMMARY OF THE INVENTION

This invention relates to a foot and leg protector comprising a rigid outer shell having a soft protective inner liner or batting. The shell and batting partially encase and generally conform about the lower leg and foot of a patient. The batting has a cut-away heel portion, and the shell is perforated in its heel area. These cut-away and perforated segments allow air to circulate about the heel.

The shell has a built-up supportive section that extends from the heel area along the lower calf portion of the shell. This built-up supportive section raises the heel area above the general level of the bed, thus preventing blockage of the perforations. This will also facilitate a freer circulation of air about the heel. This will result in a more rapid recuperation of a ducubitutus sore.

The liner has straps that project through slots in the shell, and wrap about the foot and leg of the patient. This slot and strap construction allows the shell and the liner to be integrally secured about the leg and foot, thus providing greater support. The liner, however, is a separate element from the shell, and is easily removed therefrom by rethreading the straps out of the slots in the shell.

In this way, the shell can be used over and over again for different patients. Each new patient will receive a new batting, which is threaded through the slots in the shell.

The straps may be secured about the leg or foot by means of clasps, buckles or a Velcro lining disposed at their ends.

A built-up rigid ridge section in the heel portion of the sheel prevents the heel of the patient from coming into contact with the shell. This will possibly prevent injury to the heel of the patient or the blocking of the perforations from inside the shell. This protective ridge section will also allow the patient to walk with the protector strapped to the leg.

It is an object of this invention to provide an improved foot and leg protector;

It is another object of the invention to provide a foot and leg protector that affords improved aeration and a freer circulation of air about the heel of the foot;

It is a further object of this invention to provide a foot and leg protector, wherein the liner and shell integrally bind themselves about the leg and foot of the patient, and wherein the liner is completely removable from the shell;

It is still another object of the invention to provide added rigid support structure in the heel area of the shell to prevent blockage of the aeration holes from within the shell.

These and other objects of this invention will become more apparent and will be better understood with reference to the following detailed description taken in conjunction with the accompanying drawings, in which:

FIG. 1 is a perspective view of the inventive foot and leg protector strapped to the foot and leg of a patient;

FIG. 2 is a sectional view of the inventive protector shown in FIG. 1; and

FIG. 3 is an enlarged cutaway view of the heel section of the inventive foot and leg protector illustrated in FIG. 1.

DETAILED DESCRIPTION

Referring to FIGS. 1 and 2, a leg and foot 10 of a patient is shown disposed within the inventive foot and leg protector 11 of this invention. The protector 11 is comprised of a rigid outer shell 12 and an inner liner 13 made from a soft protective batting.

The liner 13 has a number of straps 14, which project through slots 15 in the shell 12, and which are wrapped about the foot and leg 10 as illustrated in FIG. 1. The straps 14 are stitch fastened to the liner 13.

The straps 14 can have complementary buckles, clasps, or Velcro fasteners (not shown) attached to their ends 16 (FIG. 2), so as to fasten themselves about the leg and foot 10.

The shell 12 has a perforated heel section 17, that allows aeration of the heel 18 (FIG. 2). In order to insure that the holes in the heel section 17 remain unblocked, and to facilitate the freer circulation of air about the heel 18, a built-up or raised supportive section 19 is provided in the calf area of shell 12. This built-up support section 19 raises the heel section 17 above the general level 20 of the bed (FIG. 2). Because the perforated section 17 is raised above the level of the bed 20, the air is free to form convective currents, which freely circulate in and out of shell 12. This is schematically shown by air current arrows 21 in FIG. 3.

Added support is given the heel 18 by means of built-up ridges 22. These ridges 22 prevent the heel 18 from coming in contact with the perforated heel section 17. The ridges 22 may also extend around the side edges of the shell 12, in an annular fashion as depicted in FIG. 3. This annular ring prevents side shifting of the heel 18 within the shell 12. The ridges 22 also provide enough support to the heel, that the patient is able to walk with the shell attached to the leg.

When an old liner 13 is desired to be removed from the shell 12, the straps 14 may be rethreaded through the slots 15, and the old liner 13 taken out. A new liner or batting 13 is easily inserted by threading the new liner straps 14 through slots 15.

The shell 12 may be molded from any suitable plastic such as polypropylene.

The batting 13 may be made from any soft cotton or nonirritating material, which will not cause the leg to sweat. In other words, the material should allow a given amount of aeration to take place about the leg.

The straps may also be fashioned as laces.

Many modifications and changes can be made to the inventive construction consistant with the spirit and scope of the invention as outlined in the aforementioned objectives.

All such changes are deemed to fall within those limits of the invention as presented by the appended claims.

What is claimed is:

1. A therapeutic foot and leg protector comprising a rigid shell and a soft protective batting disposed within said shell, said shell and said batting partially encasing and generally conforming about a lower portion of a leg and a foot of a patient disposed therein, means defining a cut-away heel portion in said batting, said shell having a perforated heel portion substantially surrounding the heel of said patient adjacent said cut-away heel portion of said batting for the purpose of aerating a sore disposed on the heel of said patient, said shell further comprising a built-up supporting section generally extending from said heel portion along a portion of the shell encasing the lower leg portion of the patient, said supporting section raising a level of said heel portion of said shell generally above a level of a bed in which the leg and shell are resting and extended, said supporting section allowing a facilitated circulation of air about the heel of said patient via the perforated heel portion of the shell, while the leg of the patient is resting and extended upon the bed, whereby a healing of said heel sore may be more aptly effected as a result of the facilitated circulation.

2. The therapeutic foot and leg protector of claim 1, wherein said shell contains a number of slots, and wherein said batting has a number of straps affixed thereto, said straps being adapted to extend through the slots in the shell and secure about the foot and leg of said patient.

3. The therapeutic foot and leg protector of claim 1, wherein said heel portion of the shell has a built-up supporting ridge disposed about and adjacent to, the heel of the patient, said supporting ridge giving rigid support about the heel of the patient so that the heel will not come in contact with the shell.

4. The therapeutic foot and leg protector of claim 1, wherein said shell is made from a plastic material.

5. The therapeutic foot and leg protector of claim 1, wherein said batting and said shell are integrally secured about the foot and the leg of the patient by means of a number of straps affixed to the batting and which project through holes disposed about the shell.

6. The therapeutic foot and leg protector of claim 5, wherein the batting is a separate element from said shell, and can be easily removed therefrom, by rethreading the straps through the holes in the shell.

7. The therapeutic foot and leg protector of claim 5, wherein said straps comprise fasteners on their ends.

8. The therapeutic foot and leg protector of claim 7, wherein the fasteners are fashioned from Velcro.

9. The therapeutic foot and leg protector of claim 7, wherein the fasteners are clasps.

10. The therapeutic foot and leg protector of claim 7, wherein the fasteners are buckles.

* * * * *